United States Patent [19]
Gerecke et al.

[11] 3,954,769
[45] May 4, 1976

[54] DIBENZO[b,f]THIEPINS

[75] Inventors: Max Gerecke, Reinach; Jean-Pierre Kaplan, Le Plessis Robinson; Emilio Kyburz, Reinach, all of Switzerland

[73] Assignee: Hoffman-La Roche Inc., Nutley, N.J.

[22] Filed: May 17, 1974

[21] Appl. No.: 471,100

Related U.S. Application Data

[63] Continuation-in-part of Ser. No. 378,731, July 12, 1973, abandoned.

[30] Foreign Application Priority Data

Mar. 30, 1973 Switzerland.......................... 4604/73
Jan. 16, 1974 Switzerland............................ 567/74

[52] U.S. Cl............................ 260/268 TR; 424/250
[51] Int. Cl.$^2$......................................... C07D 295/08
[58] Field of Search............................. 260/268 TR

[56] References Cited
UNITED STATES PATENTS

| | | |
|---|---|---|
| 3,563,993 | 2/1971 | Schindler et al............... 260/268 TR |
| 3,583,989 | 6/1971 | Fouche et al................. 260/268 TR |
| 3,600,391 | 8/1971 | Mastursi et al............... 260/268 TR |
| 3,681,354 | 8/1972 | Mastursi et al............... 260/268 TR |
| 3,699,104 | 10/1972 | Schindler et al............. 260/268 TR |
| 3,725,409 | 4/1973 | Protiva et al. ................ 260/268 TR |
| 3,787,444 | 1/1974 | Gosteli......................... 260/268 TR |

FOREIGN PATENTS OR APPLICATIONS 1,093,910    12/1967   United Kingdom

OTHER PUBLICATIONS

Umio et al., Chemical Abstracts, Vol. 75, pp. 76847a and 76849c (1971).

Primary Examiner—Joseph A. Narcavage
Assistant Examiner—Jose Tovar
Attorney, Agent, or Firm—Samuel L. Welt; George M. Gould; William G. Isgro

[57] ABSTRACT

Compounds of the formulas

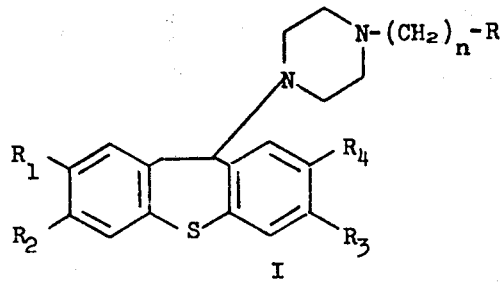

and

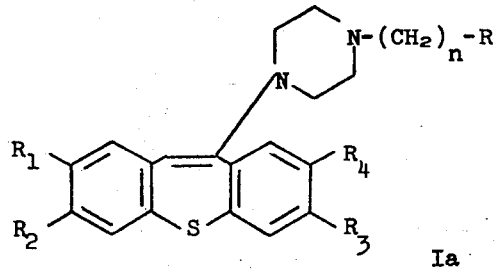

wherein R, $R_1$, $R_2$, $R_3$, $R_4$ and n are as hereinafter set forth, are described. The compounds of formulas I and Ia are prepared inter alia by reacting the corresponding dibenzo[b,f]thiepin and the corresponding piperazine compound. The end products are useful as neuroleptic agents.

9 Claims, No Drawings

DIBENZO[b,f]THIEPINS

CROSS-REFERENCE TO RELATED APPLICATIONS

This application is a continuation-in-part of application Ser. No. 378,731, filed July 12, 1973, now abandoned.

BRIEF SUMMARY OF THE INVENTION

The invention relates to tricyclic compounds of the formulas

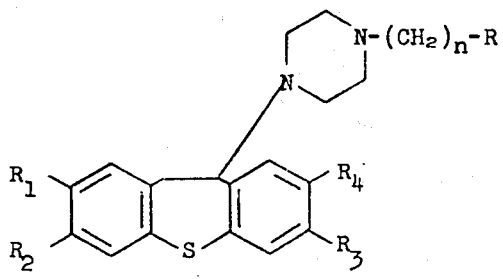

I and

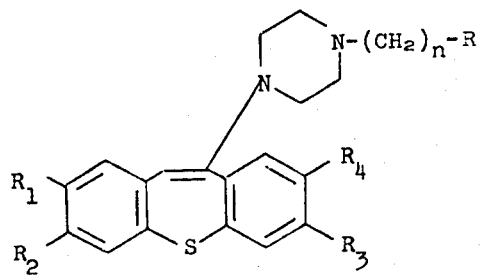

Ia wherein $n$ is an integer from 1 to 3; R is hydrogen or, when n is 2 or 3, is also hydroxy or an alkanoyloxy group of 2–18 carbon atoms, and wherein further one of $R_1$ and $R_2$ is hydrogen and the other is methyl, methoxy, methylthio, dimethylsulfamoyl, chloro or trifluoromethyl and one of $R_3$ and $R_4$ is hydrogen, and the other is methyl, methoxy, methylthio, dimethylsulfamoyl or trifluoromethyl, and pharmaceutically acceptable acid addition salts thereof. The end products are useful as neuroleptic agents.

DETAILED DESCRIPTION OF THE INVENTION

The invention relates to compounds of the formulas

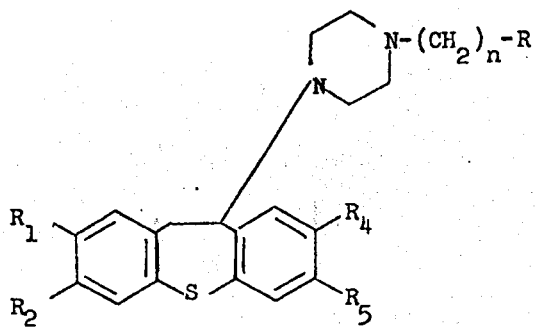

I and

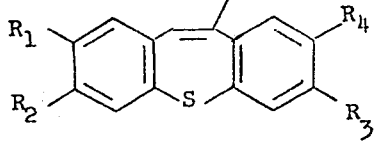

Ia wherein $n$ is 1, 2 or 3; R is hydrogen, or, when $n$ is 2 or 3, is also hydroxy, or an alkanoyl group of 2–18 carbon atoms; one of $R_1$ and $R_2$ is hydrogen and the other is methyl, methoxy, methylthio, dimethylsulfamoyl, chloro or trifluoromethyl; and one of $R_3$ and $R_4$ is hydrogen and the other is methyl, methoxy, methylthio, dimethylsulfamoyl or trifluoromethyl, and pharmaceutically acceptable acid addition salts thereof. The end products are useful as neuroleptic agents.

As used herein, the term "alkanoyloxy" denotes a straight chain or branched chain group. Exemplary of such groups are acetoxy, pivaloyloxy, pentanoyloxy, and the like. Preferred are those groups wherein the alkanoyloxy is a long chain group; preferably from 6–18 carbon atoms, for example, hexanoyloxy, heptanoyloxy, octanoyloxy, nonanoyloxy, decanoyloxy, undecanoyloxy, dodecanoyloxy, tetradecanoyloxy, hexadecanoyloxy, octadecanoyloxy, or the like.

It has been discovered that the compounds of formulas I and Ia of the invention and their pharmaceutically acceptable acid addition salts demonstrate a strong central depressant and neuroleptic activity. They can, therefore, for example, be utilized for the treatment of acute or chronic schizophrenia, as well as tranquilizers. Advantageously, compounds of the invention demonstrate no or only weak cataleptic side effects, so that no or only significant motor disturbances are observed. Preferred compounds of the invention are those of formula I, as well as their salts with pharmaceutically acceptable acids.

A preferred group of the invention comprises the compounds of formulas I and Ia, wherein $R_2$ and $R_3$ are hydrogen, $R_1$ is methoxy and $R_4$ is methylthio, as well as their salts with pharmaceutically acceptable acids. Another preferred group of the compounds of the invention are those of formulas I and Ia wherein the group $-(CH_2)_n-R$ is methyl or 3-hydroxypropyl, as well as the pharmaceutically acceptable salts of such compounds. A preferred compound of the invention is 1-[10,11-dihydro-2-methoxy-8-(methylthio)-dibenzo[b,f]thiepin]-10-yl-4-methylpiperazine and salts thereof with pharmaceutically acceptable acids.

The 10,11-saturated compounds of formula I and their addition salts with pharmaceutically acceptable acids can be prepared according to the processes hereinafter described:

a. A compound of the formula

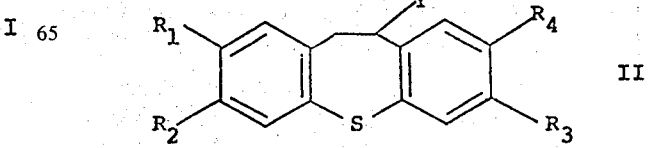

II wherein R₁, R₂, R₃ and R₄ are as hereinbefore described, and Y is a leaving group, is reacted with a compound of the formula

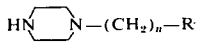  III wherein n and R are as hereinbefore described; or b. A compound of the formula

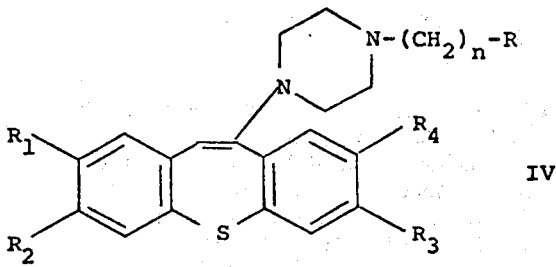  IV wherein R, R₁, R₂, R₃, R₄ and n are as hereinafter described; is reduced; or c. A compound of the formula

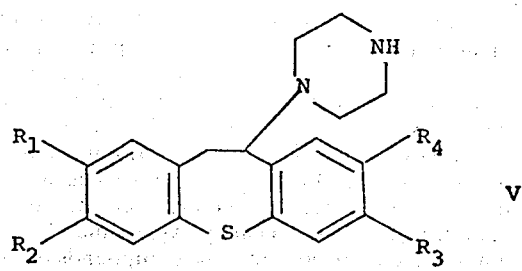  V wherein R₁, R₂, R₃ and R₄ are as hereinbefore described, is reacted with ethylene oxide, propylene oxide or a compound of the formula

  Y—(CH₂)ₙ—R   VI wherein Y, n and R are as hereinbefore described;

d. For the preparation of compounds of formula I wherein R is an alkanoyloxy group with up to 18 carbon atoms, a compound of the formula

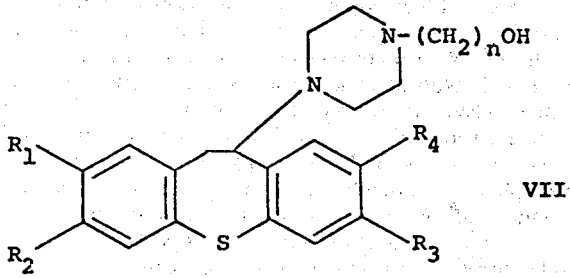  VII wherein R₁, R₂, R₃, R₄ and n are as hereinbefore described, is reacted with an acid of the formula

  R₅COOH   VIII wherein R₅ is lower alkyl of up to 17 carbon atoms, or is reacted with a reactive derivative of such an acid, and if desired, the obtained products can be converted to their pharmaceutically acceptable acid addition salts.

The 10,11-unsaturated compounds of formula Ia and their salts with pharmaceutically acceptable acids can be prepared by a process as hereinafter described, that is, a compound of the formula

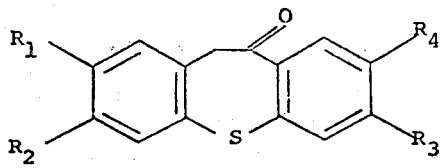  IX wherein R₁, R₂, R₃ and R₄ are as hereinbefore described, is reacted with a compound of the formula

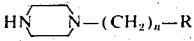  III wherein n and R are as hereinbefore described.

If desired, a compound of formula Ia, wherein R is hydroxy, can be esterified, and if desired, the resulting product can be converted to a pharmaceutically acceptable acid addition salt.

The leaving group Y of the starting material of formula II is preferably halogen or alkyl-substituted or aryl-substituted sulfonyloxy. Preferably, the alkyl group of the sulfonyloxy substituent is lower alkyl, such as methyl, and preferably the aryl group of the sulfonyloxy substituent is phenyl or p-tolyl. The halogen substituent is preferably chlorine or bromine.

The Y group of the starting material of formula II can, for example, be introduced in the following manner:

When Y is to be halogen, the corresponding 10-hydroxycompound is reacted with an appropriate halogenating agent, for example, thionyl chloride, thionyl bromide, or with a hydrogen halide in the presence of a dehydrating agent, for example, hydrogen chloride and calcium chloride.

When Y is to be alkyl-substituted or aryl-substituted sulfonyloxy, the corresponding 10-hydroxy compound is reacted with an alkyl-subsituted or aryl-substituted sulfonic acid halide, for example, the chloride.

If desired, the esters of formula III can be prepared by reacting the corresponding N-(hydroxyalkyl)-piperazine of formula III wherein the second nitrogen is protected, for example, by benzyl or benzyloxycarbonyl, with the corresponding alkanecarboxy acid halide and subsequent hydrogenolytic cleavage of the protecting group.

The aforementioned reaction of the compounds of formula II and III in accordance with the invention can be conducted without the addition of a solvent. If, however, a solvent is utilized, it preferably is an organic solvent, for example, an aromatic hydrocarbon such as benzene or toluene, a lower alkanol such as methanol or ethanol, a chlorinated hydrocarbon such as methylene chloride, trichloroethylene, chloroform, carbon tetrachloride or chlorobenzene, an aliphatic or cyclic ether such as diethyl ether, tetrahydrofuran or dioxane, or dimethylformamide or dimethylsulfoxide. The reaction temperature suitably is in the range of from about 30° to about 200°; preferably, the temperature of the reaction is in the range of from about 60° to about 150°. Advantageously, the reaction is carried out in the presence of an acid-binding agent, for example, in the presence of an alkali carbonate such as potassium carbonate or in the presence of an excess of the compound of formula III.

The starting enamines of formula IV are likewise end products of formula Ia. The enamines of formula IV are prepared in accordance with the invention by reacting the corresponding 10-oxo compound of formula IX with a compound of the above formula III. For example, the reaction can be carried out in the presence of a strong acid in an aromatic solvent with heating, for example, at a temperature in the range of from about 80° to about 150°. As the acid, there can be utilized, for example, mineral acids such as sulfuric acid or hydrochloric acid or a strong organic acid such as methanesulfonic acid or toluenesulfonic acid. As the aromatic solvents, there can be utilized, for example, preferably, benzene, toluene, or o-, m- or p-xylene. By heating, there is formed an azeotrope between the solvent and the water which is formed in the reaction, which can be distilled. The water which is formed can also be removed by the addition of a dehydrating agent such as titanium tetrachloride or the like.

An obtained enamine alcohol of formula IV, that is, a compound of formula IV, wherein R is hydroxy, can be converted to the corresponding ester of formula IV, preferably by reacting the enamine alcohol of formula IV with the corresponding alkane carboxylic acid in the presence of a non-acidic dehydrating agent, for example, dicyclohexylcarbodiimide or carbonyldiimidazole.

In accordance with the invention, the reduction of enamines of formula IV is preferably carried out by treatment with an alkali metal borohydride in the presence of a strong acid. As the alkali metal borohydride, preferably there can be used sodium or potassium borohydride, especially sodium borohydride. It is also possible to utilize lithium borohydride. The strong acid can be an organic or an inorganic acid. As an organic acid, there can be utilized a straight or branched chain lower mono- or dicarboxylic acid with up to 4 carbon atoms, which can be substituted by halogen, for example, formic acid, acetic acid, trichloroacetic acid, trifluoroacetic acid, propionic acid, isobutyric acid, oxalic acid, and the like. Preferred is acetic acid; especially preferred is oxalic acid. As the inorganic acid, there can be utilized, for example, sulfuric acid, hydrohalic acid; especially hydrochloric acid, and the like. A preferred inorganic acid is concentrated sulfuric enamines of The enaminesof formula IV are unstable in the presence of water. It is therefore indicated that the reduction suitably can be carried out in the absence of water. The reaction preferably is carried out in anhydrous acid, or only in such acids where should they contain some water, this water is not released, for example, concentrated sulfuric acid. The reaction with the alkali metal borohydride and a strong acid can advantageously be carried out in an ether such as diethyl ether, tetrahydrofuran, dioxane, diethyleneglycol-dimethyl ether (diglyme) or dimethoxyethane, at a temperature in the range of between about room temperature and the reflux temperature of the reaction mixture. Preferably, the reaction is carried out at the reflux temperature. In accordance with the invention, the reduction of an enamine of formula IV can also be carried out by other methods, for example, by treatment with formic acid or with zinc and acetic acid. The foregoing reaction is conveniently carried out at a temperature between about room temperature and the reflux temperature of the solvent; preferably at the reflux temperature.

The starting materials of formula IX as well as the corresponding 10-hydroxy compounds referred to herein are known compounds or can be prepared according to known procedures.

The starting compounds of formula V can be prepared, for example, by the reaction of a compound of formula II with a mono-N-protected piperazine such as N-carbethoxy-piperazine. The condensation product is made alkaline with the aid of, for example, an aqueous alkali.

An ester of formula VI can be prepared from the corresponding hydroxy alkyl compound of formula VI by reaction with the corresponding alkanecarboxylic acid halide.

In accordance with the invention, the reaction of a starting material of formula V with ethyleneoxide, propyleneoxide or a compound of formula VI is carried out conveniently in an inert organic solvent such as in an aromatic hydrocarbon, for example, benzene or toluene, a chlorinated hydrocarbon, for example, chloroform or the like, an ether, for example, dioxane or dimethoxyethane, a lower alkanol such as methanol or ethanol, a ketone such as acetone or methylethyl ketone, or dimethylformamide or dimethylsulfoxide. The temperature of the reaction mixture is preferably in the range of from about room temperature to about the boiling point of the reaction mixture. When utilizing a starting material of formula VI, the reaction favorably is conducted in the presence of an acid-binding agent, for example, in the presence of an alkali metal carbonate such as sodium or potassium carbonate, or in the presence of an inert organic base such as triethylamine. As the acid-binding agent there can likewise be utilized an excess of the starting material of formula V.

In accordance with the invention, the esterification of a starting material of formula VII with an acid of formula VIII can be carried out conveniently at a temperature in the range of from about 50° to about 150° with a reactive derivative of a lower-alkanecarboxylic acid, for example, with the corresponding acid chloride or acid anhydride. The esterification can also be carried out by reaction with an alkanecarboxylic acid in the presence of a strong acid catalyst such as sulfuric acid or p-toluenesulfonic acid, or in the presence of a dehydrating agent, for example, dicyclohexylcarbodiimide or carbonyldiimidazole. Preferably, the etherification is conducted in an organic solvent, for example, benzene, toluene or pyridine.

The obtained bases of formulas I and Ia form salts with inorganic as well as with organic acids, for example, with hydrohalic acids such as hydrochloric acid, hydrobromic acid or hydroiodic acid, with other mineral acids such as sulfuric acid, phosphoric acid or nitric acid, also with organic acids such as acetic acid, citric acid, camphorsulfonic acid, methanesulfonic acid, toluenesulfonic acid, salicyclic acid, ascorbic acid, maleic acid, mandelic acid, and the like. Preferred salts are those formed with hydrohalic acids and especially preferred are hydrochloric acid and maleic acid. The pharmaceutically acceptable acid addition salts, preferably can be prepared in an inert solvent, for example, ethanol, acetone or acetonitrile, by treating the free base with the corresponding anhydrous acid.

The bases of formulas I and Ia are crystalline, solid substances which are relatively soluble in dimethylsulfoxide, dimethylformamide or in chlorinated hydrocarbons such as chloroform, methylene chloride or in an alkanol such as methanol or ethanol and are relatively insoluble in water.

The pharmaceutically acceptable acid addition salts of the bases of formulas I and Ia are crystalline, solid substances. They are freely soluble in dimethylsulfoxide and dimethylformamide, in alkanols such as methanol or ethanol, and also in chloroform, methylene chloride and water. The pharmaceutically acceptable addition salts of the bases of formulas I and Ia are relatively insoluble in benzene, ether and petroleum ether.

In order to show the pharmacological action of the compounds of the invention, representative members of the compounds of the invention were submitted to the following tests:

I. Determination of cataleptic effect (undesired side effect)

A cataleptic effect ("wax-like rigidity", that is, abnormally long retention of an enforced body position) is considered to be a disturbing side effect with central depressants and neuroleptically active compounds and indicates motor disturbances. To prove the lack of cataleptic activity, representative samples of the end products of the invention were administered intraperitoneally to rats. The following compounds were tested:

Product A: 1-[10,11-dihydro-2-methoxy-8-(methylthio)-dibenzo[b,f]thiepin-10-yl]-4-methylpiperazine maleate;

Product B: 1-[10,11-dihydro-2-methyl-8-(methylthio)-dibenzo[b,f]thiepin-10-yl]-4-methylpiperazine maleate.

The foregoing compounds were compared to chlorpromazine, a well-known central dependent, especially well known as a neuroleptic agent.

The test animals are considered to be cataleptic when the homolateral extremities remain in the crossed position for at least 10 seconds. The number of cataleptic animals is recorded every 30 minutes over a 6-hour period. The $ED_{50}$ is the dose at which 50% of the animals are cataleptic.

RESULTS:

| Product | $ED_{50}$ mg/kg. |
|---|---|
| 1-[10,11-dihydro-2-methoxy-8-(methylthio)-dibenzo[b,f]thiepin-10-yl]-4-methylpiperazine maleate (Product A) | >100 |
| 1-[10,11-dihydro-2-methyl-8-(methylthio)-dibenzo[b,f]thiepin-10-yl]-4-methylpiperazine maleate (Product B) | 25 |
| Chlorpromazine | 6 |

The data of the table demonstrate that no cataleptic effect is produced by Product A of the invention, as compared to chlorpromazine, which does demonstrate cataleptic effects. Product B produces a considerably lower cataleptic effect than chlorpromazine.

II. Determination of Homovanillinic Acid

To demonstrate the central depressant effect, especially the neuroleptic effect of the products of the invention, representative compounds were utilized in the following test:

Two hours prior to being killed, rats are injected with the test substance.

Thereafter, the homovanillinic acid is extracted from the supernatant portion of a homogenous mixture of the brains into butyl acetate and later into aqueous solution and is oxidized with potassium ferric cyanide to a fluorescent dimer. From an increased concentration of homovanillinic acid (HVA), it can be demonstrated that the test substance works the same as chlorpromazine, that is, it increases the turnover of dopamine in the basal ganglions. The homovanillinic acid titer in untreated rats is arbitrarily set at 100%.

| Product | Dose mg/kg. p.o. | Increase in HVA, % |
|---|---|---|
| 1-[10,11-dihydro-2-methoxy-8-(methylthio)-dibenzo[b,f]thiepin-10-yl]-4-methylpiperazine (Product A) | 50 | 185 |
| 1-[10,11-dihydro-2-methyl-8-(methylthio)-dibenzo[b,f]theipin-10-yl]-4-methylpiperazine maleate (Product B) | 50 | 320 |
| Chlorpromazine | 20 | 320 |

In this test, Product B demonstrates an activity which is nearly as potent as that of chlorpromazine and is thus superior to chlorpromazine due to the lower cataleptic side effect (cf. above). Although Product A is somewhat less active than chlorpromazine it is superior to the latter due to complete absence of cataleptic side effect (cf. above).

III. Determination of toxicity

The data for toxicity in mice (24-hour-values) show that products A and B are superior to chlorpromazine:

| Product | $ED_{50}$ mg/kg p.o. |
|---|---|
| 1-[10,11-dihydro-2-methoxy-8-(methylthio)-dibenzo[b,f]thiepin-10-yl]-4-methylpiperazine maleate (Product A) | 1875 |
| 1-[10,11-dihydro-2-methyl-8-(methylthio)-dibenzo[b,f]thiepin-10-yl]-4-methylpiperazine maleate (Product B) | 450 |
| Chlorpromazine | 200 |

The compounds of the invention, i.e., the compounds of formulas I and Ia can be used in the form of pharmaceutical preparations, which contain them or their salts in admixture with organic or inorganic pharmaceutically inert carriers suitable for enteral and parenteral application such as, for example, water, gelatin, gum arabic, lactose, starches, vegetable oils, polyalkyleneglycols, and the like. The pharmaceutical preparations can be in solid form, for example, tablets, dragees, suppositories or xcapsules or in capsules form, for example, as solutions, suspensions or emulsions. The preparations may be sterilized and/or contain additives such as preservatives, stabilizers, wetting or emulsifying agents or salts for varying the osmotic pressure. The pharmaceutical preparations can also contain additional therapeutically active substances.

Preferably, the pharmaceutical dosage forms contain from about 1 to about 200 mg. of a compound of formula I or Ia or an equivalent amount of its respective salts. Preferably, the oral dosage range is between about 0.1 mg/kg. per day to about 7.5 mg/kg. per day. A preferable dosage range for parenteral preparations is between about 0.01 mg/kg. per day to about 0.75 mg/kg. per day. It is understood, however, that the above-mentioned ranges can be varied according to the individual needs and the prescription of the practitioner.

As is evident, the compounds of formulas I and Ia and their pharmaceutically acceptable acid addition salts have effects qualitatively similar to those of chlorpromazine, known for its therapeutic uses and properties. Thus, the compounds of the invention demonstrate a pattern of activity associated with neuroleptic agents of known efficacy and safety.

The following Examples further illustrate the invention. All temperatures are in degrees Centigrade, unless otherwise mentioned.

EXAMPLE 1

Preparation of
1-(10,11-dihydro-3-methoxy-8-(methylthio)dibenzo[b,f]-thiepin-10-yl)-4-methyl-piperazine 17.7 G. of 10-chloro-10,11-dihydro-3-methoxy-8-chloro-(methylthio)-dibenzo[b,f]thiepin are heated together with 22 g. of N-methylpiperazine in a flask for 10 minutes at an outside temperature of 120°–130°. Subsequently, the reaction mixture is cooled by pouring water over it and is extracted with ether. The organic phase is washed with water and treated with 2N hydrochloric acid, whereby a precipitate forms. The total mixture obtained is washed with ether, made alkaline and subsequently extracted with ether. The organic phase is washed with water, dried over sodium sulate and evaporated. The resulting residue is chromatographed over aluminum oxide with toluene. The so-obtained 1-(10,11-dihydro-3-methoxy-8-(methylthio)-dibenzo[b,f]-thiepin-10-yl)-4-methylpiperazine is reacted with maleic acid whereby the maleate is formed. The maleate is recrystallized from ethanol/ether and has a melting point of 117°–119°.

The starting material 10-chloro-10,11-dihydro-3-methoxy-8-(methylthio)-dibenzo[b,f]thiepin can be prepared as follows:

150 G. of 4-methoxy-anthranillic acid is suspended in 2 l. of water and 80 ml. of concentrated hydrochloric acid at 0°. To this mixture is added dropwise with stirring, a solution of 62 g. of sodium nitrite in 130 ml. of water at 0°–5° over a period of 30 minutes. The resulting diazonium salt solution is stirred at 0°–5° for an additional 15 minutes. Subsequently, there is added a solution of 164 g. of potassium iodide in 700 ml. of 5N sulfuric acid at a temperature of 3°–6° over a 45 minute period. The resulting mixture is mixed at room temperature for 30 minutes and subsequently heated slowly at reflux temperature. After heating at reflux for 2 hours, the mixture is cooled to room temperature. The separated brown crystals are filtered and washed neutral with water. The filter cake is dried under reduced pressure, whereby there is obtained as brown crystals 2-iodo-4-methoxy-benzoic acid having a melting point of 174°.

411 G. of 2-iodo-4-methoxy-benzoic acid, 4 l. methanol and 400 ml. of concentrated sulfuric acid are heated at reflux for 4 hours. The solution is then evaporated under reduced pressure, treated with water, and extracted with ether. The organic phase is then washed with aqueous sodium thiosulfate solution and aqueous sodium bicarbonate solution and subsequently dried over sodium sulfate. The solution is filtered, evaporated under reduced pressure and distilled. There is obtained the 2-iodo-4-methoxy-benzoic acid methyl ester, having a boiling point of 95°–98°/0.04 mm.

205 G. of 2-iodo-4-methoxy-benzoic acid methyl ester, 400 ml. of methanol, 390 ml. of water and 95 g. of potassium hydroxide are reacted for 30 minutes at 48°. Subsequently, the solution is concentrated under reduced pressure and acidified with aqueous hydrochloric acid. The resulting yellow crystalline 2-iodo-4-methoxy-benzoic acid is filtered, washed neutral with water and dried. The resulting compound melts at 185°.

A solution of 170 g. of potassium hydroxide in 1.6 l. of water is reacted under an atmosphere of nitrogen with 102 g. of 4-(methylthio)-(thiophenol) at 50°. The resulting mixture is subsequently stirred for an additional 15 minutes. The mixture is reacted with 2.4 g. of copper powder and 180 g. of 2-iodo-4-methoxy-benzoic acid and heated under reflux conditions for 7 hours. The reaction mixture is filtered hot, acidified with concentrated hydrochloric acid, cooled and filtered. The residue is washed with water and dried under reduced pressure, whereby there is obtained 4-methoxy-6-{[4'-(methylthio)-phenyl]-thio} benzoic acid having a melting point of 202°–203°.

190 G. of 4-methoxy-6-{[4'-(methylthio)-phenyl]thio}-benzoic acid in 1.8 l. of absolute tetrahydrofuran was treated dropwise under an atmosphere of nitrogen and under reflux conditions with 850 ml. of a 70% solution of sodium dihydro-bis-(2-methoxy-ethoxy)-aluminate solution in benzene. The reaction mixture is then heated under reflux conditions for an additional 30 minutes. After cooling to 5°, the reaction mixture is acidified with 500 ml. of 3N hydrochloric acid and with concentrated hydrochloric acid and thereafter extracted with ether. The organic phase is washed with water, 2N aqueous sodium hydroxide solution and again with water and dried over sodium sulfate, filtered and evaporated, whereby there is obtained 4-methoxy-6-{[4'-(methylthio)-phenyl]thio}-benzyl alcohol as a brown oil.

165 G. of 4-methoxy-6-{[4'-(methylthio)-phenyl]thio}-benzyl alcohol are dissolved in 500 ml. of absolute benzene and heated under reflux conditions. The resulting solution is treated dropwise over a period of 45 minutes with 62 ml. of thionyl chloride and subsequently heated over a period of 30 minutes. The reaction mixture is evaporated under reduced pressure. The residue is extracted three times with benzene. From the benzene solution there is obtained 4-methoxy-6-{[4'-(methylthio)-phenyl] thio}-benzyl chloride as a dark brown oil. 51 G. of potassium cyanide in 110 ml. of water are heated with 186 g. of 4-methoxy-6-{[4'-(methylthiio)-phenyl] -thio}-benzyl chloride in 270 ml. of ethanol under reflux conditions over a period of 9 hours. The ethanol is distilled under reduced pressure, thereafter the residue is diluted with water and extracted with ether. The ethereal extract is washed with water, dried over sodium sulfate and evaporated, whereby there is obtained 4-methoxy-6{[4'-(methylthio)-phenyl]-thio}-phenylacetonitrile as a dark brown oil.

160 G. of 4-methyl-6{[4'-(methylthio)-phenyl]-thio}-phenylacetonitrile, 330 ml. of ethanol, 162 g. of potassium hydroxide and 330 ml. of water are heated under reflux conditions for 8 hours. Thereafter, the ethanol is evaporated under reduced pressure. The resulting residue is washed twice with 2 l. of water. The aqueous solution is extracted with ether and the ether extract is discarded. The aqueous solution is cooled and acidified with concentrated hydrochloric acid. The solution thereafter is extracted with benzene and the benzene phase washed with water, dried over sodium sulfate, filtered and evaporated, whereby there is obtained 4-methoxy-6{[4'-methylthio)-phenyl]-thio}-phenylacetic acid which upon recrystallization from benzene/hexane has a melting point of 125°.

29.3 G. of 4-methoxy-6-{]4'-(methylthio)-phenyl]-thio}-phenylacetic acid is stirred with 150 g. of polyphosphoric acid in 660 ml. of toluene under reflux conditions for 17 hours. The reaction mixture is cooled to about 60° and the toluene solution is decanted. The residue is treated with toluene and heated with stirring. The aqueous residue is treated with ice and water and extracted with toluene. The so-obtained toluene solution is thereafter treated with water and aqueous sodium hydroxide and washed with aqueous sodium hydroxide solution, dried over sodium sulfate and concentrated under reduced pressure, whereby there is obtained 3-methoxy-8-(methylthio)-dibenzo [b,f]thiepin-10(11H)-one as a red oil. Upon recrystallization from acetone/hexane there is obtained from the red oil a crystalline product having a melting point of 127°.

17.8 G. of 3-methoxy-8-(methylthio)-dibenzo [b,f]b,f]thiepin-[b,f](11H)-one is suspended in 150 ml. of ethanol and reacted with 38 g. of sodium borohydride. The reaction mixture is stirred for 90 minutes, and subsequently treated with water and extracted with ether. The organic phase is washed with water, dried over magnesium sulfate and evaporated, whereby there is obtained 10,11-dihydro-3-methoxy-8-(methylthio)-dibenzo [b,f]thiepin-10-ol having a melting point of 122°–124°.

15.7 G. of 10,11-dihydro-3-methoxy-8-(methylthio)-dibenzo ]thiepin-10-ol, 250 ml. of benzene and 6 g. of finely pulverized calcium chloride are saturated with hydrochloric acid gas over a period of 2½ hours at 15° and subsequently stirred for an additional 3 hours. After the addition of 0.8 g. of activated charcoal, the mixture is filtered and washed with benzene. The benzene phase is evaporated under reduced pressure, whereby there is obtained 10-chloro-10,11-dihydro-3-methoxy-8-(methylthio)-dibenzo [b,f]thiepin, having a melting point of 120°–123°.

EXAMPLE 2

In a manner similar to that described in Example 1, from 10-chloro-10,11-dihydro-2-methoxy-8-(methylthio)-dibenzo [b,f]thiepin and N-methylpiperazine, there can be obtained 1-[10,11-dihydro-2-methoxy-8-(methylthio)-dibenzo[b,f]thiepin-10-yl]-4-methylpiperazine as the maleate having a melting point of 169°.

The starting material 10-chloro-10,11-dihydro-2-methoxy-8-(methylthio)-dibenzo[b,f]thiepin can be obtained from 2-iodo-5-methoxy-benzoic acid and 4-(methylthio)-(thiophenol) in a similar manner to that described in Example 1. There are obtained the folowng intermediates:

3-methoxy-6-{[4'-(methylthio)-phenyl]thio}-benzoic acid having a melting point of 138°–139°;
3-methoxy-6-{[4'-(methylthio)-phenyl]thio}-benzyl alcohol having a melting point of 75°;
3-methoxy-6-{[4'-(methylthio)-phenyl]thio}-benzyl chloride as a dark brown oil;
3-methoxy-6-{[4'-(methylthio)-phenyl]-thio}-phenylacetonitrile as a dark brown oil;
3-methoxy-6-{[4'-(methylthio)-phenyl] thio}-phenylacetic acid having a melting point of 100°–101°;
2-methoxy-8-(methylthio)-dibenzo[b,f]thiepin-10(11H)-one having a melting point after recrystallization from ethanol of 129°; and
10,11-dihydro-2-methoxy-8-(methylthio)-dibenzo[b,f]thiepin-10-ol having a melting point of 95°.

The resulting 10-chloro-10,11-dihydro-2-methoxy-8-(methylthio)-dibenzo [b,f]-thiepin melts at 105°.

EXAMPLE 3

Preparation of
1-{2-methyl-8-(methylthio)dibenzo[b,f]thiepin-10-yl}-4-methylpiperazine To 28.6 g. of 2-methyl-8-(methylthio)-dibenzo[b,f]-thiepin-10(11H)-one and 50 ml. of N-methylpiperazine in 300 ml. absolute benzene there are added, in an argon atmosphere, within the course of 1 hour 9.3 ml. of titanium tetrachloride in 150 ml. of benzene. The reaction mixture is heated 15 hours under reflux conditions and subsequently poured onto a saturated aqueous sodium bicarbonate solution and extracted with a mixture of chloroform and benzene. The organic phase is washed with water, dried and evaporated to dryness. Upon crystallization from methanol, 1-{2-methyl-8-(methylthio)dibenzo [b,f]thiepin-10-yl}-4-methylpiperazine, having a melting point of 154°–155° is obtained. The maleate is recrystallized from acetone and melts 230°–231°.

In an analogous manner, 1-(2-chloro-8-methylthio-dibenzo-[b,f]thiepin-10-yl)-4-methylpiperazine is prepared, which has a melting point of 155°–157°C. after recrystallization from methanol.

The starting material 2-methyl-8-(methylthio)dibenzo[b,f]-thiepin-10(11H)-one can be obtained from 2-iodo-5-methyl-benzoic acid and 4-(methylthio)-(thiophenol) in a similar manner to that described in Example 1. There are obtained the following intermediates:

3-methyl-6-{[4'-(methylthio)-phenyl]-thio}-benzoic acid having a melting point of 155°–158°;
3-methyl-6-{[4'-(methylthio)-phenyl]-thio}-benzyl alcohol as crystals;
3-methyl-6-{[4'-(methylthio)-phenyl]-thio}-benzyl chloride as a brown oil;
3-methyl-6-{[4'-(methylthio)-phenyl]-thio}-phenyl acetonitrile as a red oil;
3-methyl-6-{[4-'-(methylthio)-phenyl]-thio}-phenyl acetic acid having a melting point of 89°–92°.

The resulting 2-methyl-8-(methylthio)dibenzo[b,f]-thiepin-10(11H)-one melts at 108°–110°.

In the same manner, there is prepared 2-chloro-8-methylthio-dibenzo[b,f]thiepin- 10(11H)-one which is used as the starting material for the manufacture of 1-(2-chloro-8-methylthio-dibenzo [b,f]thiepin-1-yl)-4-methylpiperazine mentioned earlier. The following intermediates are obtained in the reaction:

3-chloro-6-[(4'-methylthio-phenyl)-thio]-benzoic acid (red), melting point 170°–180°C.;
3-chloro-6-[(4'-methylthio-phenyl)-thio]-benzyl alcohol (red-brown oil);
3-chloro-6-[(4'-methylthio-phenyl)-thio]-benzyl chloride (red-brown oil);
3-chloro-6-[(4'-methylthio-phenyl)-thio]-phenylacetonitrile (dark, red-brown oil);
3-chloro-6-[(4'-methylthio-phenyl)-thio]-phenylacetic acid, melting point 112°–113°C. after recrystallization from ethyl acetate/petroleum ether (low boiling).

The 2-chloro-8-methylthio-dibenzo[b,f]thiepin-10(11)-one obtained melts at 173°–175°C. after recrystallization from xylene.

EXAMPLE 4

Preparation of
1-{10,11-dihydro-2-methyl-8-(methylthio)-dibenzo-[b,f]thiepin-10-yl}-4-methylpiperazine 16 G. of 1-{2-methyl-8-(methylthio)-dibenzo[b,f]-thiepin-10-yl}-4-methylpiperazine are dissolved in 200 ml. of diglyme and, at room temperature under an atmosphere of nitrogen, treated with 11.5 g. of sodium borohydride. The reaction mixture is stirred for 30 minutes and the within 45 minutes treated with a solution of 60 g. of oxalic acid in 300 ml. of diglyme. Subsequently, the mixture is heated for 2 hours at 100°, evaporated under reduced pressure and equilibrated between 2N aqueous sodium hydroxide and chloroform. The chloroform extracts are washed with water, dried and purified on a column containing 300 g. of aluminum oxide (activity grade II). 1-{10,11-dihydro-2-methyl-8-(methylthio)dibenzo[b,f]thiepin-10-yl}-4-methylpiperazine is obtained as a light oil. The corresponding maleate is precipitated from acetone and melts at 193°–194°.

In an analogous manner, 1-(2-chloro-10,11-dihydro-8-methylthio-dibenzo[b,f]thiepin-10-yl)-4-methylpiperazine is prepared from 1-(2-chloro-8-methylthiodibenzo[b,f]thiepin-10-yl)-4-methylpiperazine. By reaction with methanesulfonic acid in methanol, the crystalline product is converted into the dimethanesulfonate which, after recrystallization from acetone, contains 1.47 percent water and has a melting point of 203°–204°C.

EXAMPLE 5

Preparation of
3-{4-(10,11-dihydro-3-methoxy-8-methylthiodibenzo[b,f]thiepin-10-yl)-1-piperazinyl}-1-propanol 12 G. of 10-chloro-10,11-dihydro-3-methoxy-8-methyltiodibenzo[b,f]thiepin in 60 ml. of chloroform are heated with 27 g. of N-(3-hydroxypropyl)-piperazine under reflux conditions for 20 hours. The chloroform is evaporated and the residue partitioned in ether and 1N sodium hydroxide. The organic phase is washed with water and treated with ethanolic hydrochloric acid. The precipitate obtained is removed by filtration and washed with ether. The filter cake is partitioned between benzene and 2N sodium hydroxide. The organic phase is washed with water, dried over sodium sulfate and evaporated. The residue obtained is chromatographed with chloroform over aluminum oxide and the 3- 4-(10,11-dihydro-3-methoxy-8-methylthio-dibenzo[b,f]thiepin-10-yl)-1-piperazinyl -1-propanol thus obtained is converted into the corresponding dihydrochloride by reaction with hydrogen chloride. The dihydrochloride is recrystallized from ethanol/ether and then melts at 214°–217°C.

In an analogous manner, 2-{4(10,11-dihydro-3-methoxy-8-methylthio-dibenzo[b,f]thiepin-10-yl)-1-piperazinyl}-1-ethanol (whose dihydrochloride melts at 222°–223°C. after recrystallization from methanol/ether) is prepared from 10-chloro-10,11-dihydro-3-methoxy-8-methylthio-dibenzo[b,f]thiepin and N-(2-hydroxyethyl)-piperazine.

EXAMPLE 6

Preparation of
1-(10,11-dihydro-3-methyl-8-methylthio-dibenzo[b,f]thiepin-10-yl)-4-methylpiperazine 10.0 G. of 10-chloro-10,11-dihydro-3-methyl-8-methylthio-dibenzo[b,f]thiepin, 300 ml. of chloroform and 9.8 g. of N-methylpiperazine are heated at reflux for 30 hours. The mixture is evaporated under reduced pressure. The residue is worked up in an analogous manner to that described in Example 1, and there is obtained 1-(10,11-dihydro-3-methyl-8-methylthio-dibenzo[b,f]-thiepin-10-yl)-4-methylpiperazine whose dimethanesulfonate crystallizes from acetone and melts at 199°–200°C.

The 10-chloro-10,11-dihydro-3-methyl-8-methylthio-dibenzo-[b,f]thiepin used as the starting material can be prepared in an analogous manner to that described in Example 1. The following intermediates are obtained in the reaction:

4-methyl-6[(4′-methylthio-phenyl)-thio]-benzoic acid having a melting point of 250°–255°C.;
4-methyl-6-[(4′-methylthio-phenyl)-thio]-benzyl alcohol (yellow oil which crystallizes on standing);
4-methyl-6-[(4′-methylthio-phenyl)-thio]-benzyl chloride (brown oil);
4-methyl-6-[(4′-methylthio-phenyl)-thio]-phenylacetonitrile (brown oil);
4-methyl-6-[(4′-methylthio-phenyl)-thio]-phenylacetic acid having a melting point of 140°–142°C. after recrystallization from acetone/petroleum ether (low boiling);
3-methyl-8-methylthio-dibenzo[b,f]thiepin-10(11H)-one having a melting point of 108°–114°C. after recrystallization from ethanol;
10,11-dihydro-3-methyl-8-methylthio-dibenzo[b,f]-thiepin-10-ol (red-brown oil).

The 10-chloro-10,11-dihydro-3-methyl-8-methylthio-dibenzo-[b,f]thiepin is obtained as a yellow, crystalline mass.

EXAMPLE 7

Preparation of
1-(2-chloro-10,11-dihydro-7-methyl-dibenzo[b,f]-thiepin-10-yl)-4-methylpiperazine 12 G. of 2,10-dichloro-10,11-dihydro-7-methyl-dibenzo[b,f]-thiepin and 12.4 g. of N-methylpiperazine are dissolved in 310 ml. of chloroform and the solution heated at reflux for 16 hours. The cooled solution is washed with 2N sodium hydroxide and water. The organic phase is decanted and extracted with a dilute methanesulfonic acid solution. The acid solution is made alkaline earth sodium hydroxide and the oil that separates is taken up in ether. The organic phase is washed with water, dried over magnesium sulfate and concentrated under vacuum, and there is obtained 1-(2-chloro-10,11-dihydro-7-methyl-dibenzo-[b,f]thiepin-10-yl)-4-methylpiperazine which melts at 136°–137.5°C. This base is converted into the dimethanesulfonate by reaction with methanesulfonic acid.

The 2,10-dichloro-10,11-dihydro-7-methyl-dibenzo[b,f]-thiepin used as the starting material can be prepared in an analogous manner to that described in Example 1 starting from 5-chloro-2-iodo-benzoic acid and 3-methyl-thiophenol. The following intermediates are obtained in the reaction:

5-chloro-2-[(3′-methyl-phenyl)-thio]-benzoic acid having a melting point of 163°–166°C.;
5-chloro-2-[(3′-methyl-phenyl)-thio]benzyl alcohol (light brown oil);
5-chloro-2-[(3′-methyl-phenyl)-thio]-benzyl chloride (brown oil);
5-chloro-2-[(3′-methyl-phenyl)-thio]-phenylacetonitrile (brown oil);
5-chloro-2-[(3′-methyl-phenyl9-thio]-phenylacetic acid having a melting point of 112°–114°C.;
2-chloro-7-methyl-dibenzo[b,f]thiepin-10(11H)-one having a melting point of 113°–115°C.;
2-chloro-10,11-dihydro-7-methyl-dibenzo[b,f]thiepin-10-ol having a melting point of 136°–138°C.

The 2,10-dichloro-10,11-dihydro-7-methyl-dibenzo[b,f]thiepin obtained melts at 145°–147°C.

The following Examples illustrate pharmaceutical preparations containing the dibenzo[b,f]thiepin derivatives of the invention.

EXAMPLE A

TABLETS

| | Per Tablet |
|---|---|
| 1-(10,11-dihydro-2-methoxy-8-methyl-thio-dibenzo[b,f]thiepin-10-yl)-4-methylpiperazine maleate | 100 mg. |
| Lactose | 202 mg. |
| Maize Starch | 80 mg. |

-continued
TABLETS

| | Per Tablet |
|---|---|
| Hydrolyzed Maize Starch | 20 mg. |
| Calcium Stearate | 8 mg. |
| Total Weight | 410 mg. |

The active ingredient, lactose, maize starch and hydrolyzed maize starch are mixed together and granulated with water to a viscous paste. The paste is passed through a sieve and subsequently dried overnight at 45°C. The dried granulate is passed through a sieve, mixed with the calcium stearate, and subsequently pressed into tablets weighing 410 mg. and about 10 mm. diameter.

EXAMPLE B

TABLETS

| | Per Tablet |
|---|---|
| 1-(10,11-dihydro-2-methoxy-8-methyl-thio-dibenzo[b,f]thiepin-10-yl)-4-methylpiperazine maleate | 25.0 mg. |
| Lactose | 114.0 mg. |
| Maize Starch | 50.0 mg. |
| Gelatinized Maize Starch | 8.0 mg. |
| Calcium Stearate | 3.0 mg. |
| Total Weight | 200.0 mg. |

The active ingredient, lactose, maize starch and gelatinized maize starch are mixed intimately with one another. The mixture is passed through a comminuting machine and subsequently moistened with water to give a thick paste. The moist mass is passed through a sieve, and the moist granulate is dried at 45°C. The dried granulate is mixed thoroughly with the calcium stearate, and then pressed into tablets weighing 200 mg. and about 8 mm. diameter.

EXAMPLE C

TABLETS

| | Per Tablet |
|---|---|
| 1-(10,11-dihydro-2-methoxy-8-methyl-thio-dibenzo[b,f]thiepin-10-yl)-4-methylpiperazine maleate | 14.5 mg. |
| Lactose | 124.5 mg. |
| Maize Starch | 50.0 mg. |
| Gelatinized Maize Starch | 8.0 mg. |
| Calcium Stearate | 3.0 mg. |
| Total Weight | 200.0 mg. |

The active ingredient, lactose, maize starch and gelatinized maize starch are mixed intimately with one another. The mixture is passed through a comminuting machine and subsequently moistened with water to give a thick paste. The moist mass is passed through a sieve, and the moist granulate is dried at 45°C. The dried granulate is mixed thoroughly with the calcium stearate and then pressed into tablets weighing 200 mg. and about 8 mm. diameter.

EXAMPLE D

TABLETS

| | Per Tablet |
|---|---|
| 1-(10,11-dihydro-2-methoxy-8-methyl-thio-dibenzo[b,f]thiepin-10-yl)-4-methylpiperazine maleate | 25.00 mg. |
| Lactose | 110 mg. |
| Maize Starch | 61.00 mg. |

-continued
TABLETS

| | Per Tablet |
|---|---|
| Talc | 3.40 mg. |
| Magnesium Stearate | 0.60 mg. |
| Total Weight | 200.00 mg. |

The ingredients are mixed intimately with one another and pressed into tablets each of 200 mg. Subsequently, they are coated with ethyl cellulose and Carbowax.

EXAMPLE E

CAPSULES

| | Per Capsule |
|---|---|
| 1-(10,11-dihydro-2-methoxy-8-methyl-thio-dibenzo[b,f]thiepin-10-yl)-4-methylpiperazine maleate | 29.0 mg. |
| Lactose | 156.0 mg. |
| Maize Starch | 30.0 mg. |
| Talc | 5.0 mg. |
| Total Weight | 220.0 mg. |

The active ingredient, lactose and maize starch are mixed intimately with one another and passed through a comminuting machine. The mixture is now mixed thoroughly with the talc and filled into hard gelatin capsules.

EXAMPLE F

CAPSULES

| | Per Capsule |
|---|---|
| 1-(10,11-dihydro-2-methoxy-8-methyl-thio-dibenzo[b,f]thiepin-10-yl)-4-methylpiperazine maleate | 25.5 mg. |
| Lactose | 159.5 mg. |
| Maize Starch | 30.0 mg. |
| Talc | 5.0 mg. |
| Total Weight | 220.0 mg. |

The active ingredient, lactose and maize starch are mixed intimately with one another and passed through a comminuting machine. The mixture is then mixed thoroughly with the talc and filled into hard gelatin capsules.

EXAMPLE G

PARENTERAL PREPARATION
Each 1 ml. ampule contains:

| | |
|---|---|
| 1-(10,11-dihydro-2-methoxy-8-methyl-thio-dibenzo[b,f]thiepin-10-yl)-4-methylpiperazine | 10.20 mg. (2 percent excess) |
| Methanesulfonic acid for injection | 2.22 mg. |
| Glucose for injection | 40.0 mg. |
| Water for injection q.s. ad | 1 ml. |

In a glass vessel, there are dissolved in 8000 ml. of water for injection with stirring at room temperature, successively:
22.2 g. of methanesulfonic acid for injection,
102 g. of active ingredient and
400 g. of glucose.
Subsequently, additional water for injection is added to a total volume of 10,000 ml. The solution is either aseptically filtered, filled into colorless ampules, gassed with nitrogen and sealed or filled into colorless ampules, gassed with nitrogen, sealed and subsequently sterilized in a current of steam or autoclaved at 120°C. for 30 minutes.

Exemplary end products encompassed by claim 1 are e.g., the following:

1-{10,11-dihydro-3-methoxy-8-(dimethylsulfamoyl)-dibenzo-[b,f]thiepin-10-yl}-4-methylpiperazine,
1-{10,11-dihydro-3-(trifluoromethyl)-8-methyl-dibenzo[b,f]-thiepin-10-yl}-4-methylpiperazine;

and their pharmaceutically acceptable acid addition salts;

the compounds corresponding to the end products of Examples 1-7 and the above compounds which are 4-(3-hydroxypropyl)-piperazines or 4-(3-decanoyloxypropyl)-piperazines instead of 4-methylpiperazines.

We claim:
1. A compound of the formula

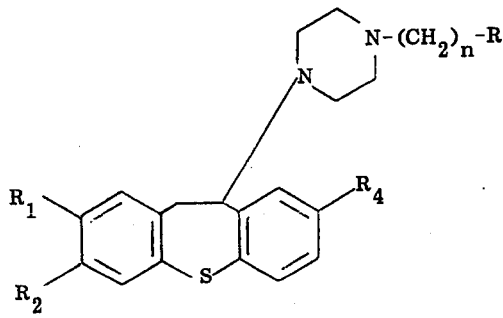

wherein $n$ is 1, 2 or 3; R is hydrogen or when $n$ is 2 or 3, is hydroxy; one of $R_1$ and $R_2$ is hydrogen and the other is methoxy; and $R_4$ is methylthio, or a pharmaceutically acceptable acid addition salt thereof.

2. A compound in accordance with claim 1, wherein $R_2$ is hydrogen.

3. A compound in accordance with claim 2, wherein the group —$(CH_2)_n$—R is methyl or 3-hydroxypropyl.

4. A compound in accordance with claim 1, 1-[10,11-dihydro-2-methoxy-8-(methylthio)-dibenzo[b,f]thiepin-10-yl]-4-methylpiperazine.

5. A compound in accordance with claim 1, wherein the group —$(CH_2)_n$—R is methyl or 3-hydroxypropyl.

6. A compound in accordance with claim 1, wherein $R_1$ is hydrogen.

7. A compound in accordance with claim 6, wherein the group —$(CH_2)_n$—R is 2-hydroxyethyl or 3-hydroxypropyl.

8. The compound in accordance with claim 1, 4-[10,11-dihydro-3-methoxy-8-(methylthio)-dibenzo[b,f]thiepin-10-yl]-1-piperazine-ethanol.

9. The compound in accordance with claim 1, 4-[10,11-dihydro-3-methoxy-8-(methylthio)-dibenzo[b,f]thiepin-10-yl]-1-piperazine-propanol.

* * * * *